United States Patent [19]

Vedage et al.

[11] Patent Number: 5,196,587
[45] Date of Patent: Mar. 23, 1993

[54] CATALYTIC HYDROGENATION OF CRUDE METHYLENE BRIDGED POLYPHENYLAMINES TO PRODUCE POLYCYCLOHEXYLAMINES

[75] Inventors: Gamini A. Vedage, Bethlehem; William W. Henderson; Bernard A. Toseland, both of Allentown, all of Pa.

[73] Assignee: Air Products and Chemicals, Inc., Allentown, Pa.

[21] Appl. No.: 699,425

[22] Filed: May 13, 1991

Related U.S. Application Data

[63] Continuation of Ser. No. 175,010, Mar. 30, 1988, abandoned.

[51] Int. Cl.$^5$ .............................................. C07C 209/00
[52] U.S. Cl. ........................................ 564/451; 564/450
[58] Field of Search .................................. 564/450, 451

[56] References Cited

U.S. PATENT DOCUMENTS

| | | | |
|---|---|---|---|
| 2,511,028 | 6/1950 | Whitman | 260/563 |
| 2,606,924 | 8/1952 | Whitman | 260/563 |
| 2,606,925 | 8/1952 | Whitman | 260/563 |
| 2,606,928 | 8/1952 | Barkdoll | 260/563 |
| 3,591,635 | 7/1971 | Farrissey | 260/563 B |
| 3,636,108 | 1/1972 | Brake | 260/563 B |
| 3,644,522 | 2/1972 | Brake et al. | 260/563 D |
| 3,697,449 | 10/1972 | Brake | 252/474 |
| 3,856,862 | 12/1974 | Chung et al. | 260/563 B |
| 3,959,374 | 5/1976 | Brennan et al. | 260/563 B |
| 4,448,995 | 5/1984 | Allen | 564/451 |

FOREIGN PATENT DOCUMENTS 066212  5/1982  European Pat. Off. .

Primary Examiner—Alan L. Rotman
Assistant Examiner—Raymond Covington
Attorney, Agent, or Firm—Russell L. Brewer; James C. Simmons; William F. Marsh

[57] ABSTRACT

This invention relates to an improved process for the catalytic hydrogenation of methylene bridged polyphenylamines using rhodium as the catalyst to produce the methylene bridged polycyclohexylamine counterparts. The improvement for hydrogenating crude methylene bridged polyphenylamines containing polyphenylamine oligomers and trace amounts of impurities, such as the formamide of the methylene bridged polyphenylamines, comprises contacting the crude polyphenylamine feed with a hydrogenation catalyst, other than rhodium, and one which is not a catalyst poison to rhodium, under conditions sufficient to at least partially hydrogenate the polyphenylamine mixture and then effecting hydrogenation of the methylene bridged polyphenylamine to the polycyclohexylamine counterpart in the presence of a rhodium catalyst. The pretreatment of the crude methylene bridged polyphenylamine feed apparently destroys the formamide derivatives and possibly other trace impurities in the mixture and thereby prevents rapid deactivation of the rhodium catalyst during hydrogenation of the aromatic ring.

16 Claims, No Drawings

CATALYTIC HYDROGENATION OF CRUDE METHYLENE BRIDGED POLYPHENYLAMINES TO PRODUCE POLYCYCLOHEXYLAMINES

This is a continuation of application Ser. No. 07/175,010 filed Mar. 30, 1988 now abandoned.

TECHNICAL FIELD

This invention pertains to an improved process for hydrogenating methylene bridged polyphenylamines to the polycyclohexylamines counterparts.

BACKGROUND OF THE INVENTION

There is substantial literature in the art with respect to the hydrogenation of methylene bridged polyphenylamines to produce polycyclohexylamine counterparts using a hydrogenation catalyst. A material for which there has been substantial hydrogenation activity effort is methylenedianiline with the end product being bis(4-aminocyclohexyl)methane; it is also called bis(para-aminocyclohexyl)methane or PACM. Some of the early work was done by Whitman and Barkdoll, et al. and their work is set forth in a series of U.S. Pat. Nos. e.g., 2,511,028; 2,606,924; 2,606,925; and 2,606,928. Basically the processes described in these patents involve the hydrogenation of methylenedianiline at pressures in excess of 200 psig, preferably in excess of 1,000 psig, at temperatures within a range of 80° to 275° C. utilizing a ruthenium catalyst for the hydrogenation. The hydrogenation is carried out under liquid phase conditions. Usually an inert organic solvent is used in the hydrogenation process. Examples of ruthenium catalysts utilized for the hydrogenation process include ruthenium oxides such as ruthenium sesquioxide and ruthenium dioxide; and ruthenium salts.

Brake, et al. continued with the development of hydrogenation process to produce PACM and they found that if the ruthenium catalyst was carried upon a support and the support alkali-moderated, the catalyst was much more active and catalytically effective in producing the desired hydrogenated PACM product. Alkali moderation was effected by contacting the catalyst and support with alkali metal hydroxide or an alkoxide; also, such alkali moderation of the catalyst could be effected prior to hydrogenation or in situ during the hydrogenation. Representative patents showing the utilization of alkali moderated ruthenium catalysts to hydrogenate methylenedianiline include U.S. Pat. Nos. 3,636,108; 3,644,522; and U.S. Pat. No. 3,697,449. Alkali metal and alkaline earth metal nitrates and sulfates have similarly been shown effective in U.S. Pat. No. 4,448,995 under high pressure (4000 psi) hydrogenation conditions.

Other catalysts have been utilized for the hydrogenation of methylenedianiline and examples are shown in U.S. Pat. No. 3,591,635 and U.S. Pat. No. 3,856,862. Both patents disclose the use of rhodium as a catalytic material and each require the use of an aliphatic alcohol as a solvent. The rhodium is alkali moderated using ammonium hydroxide as a pretreatment or by carrying out the reaction in the presence of ammonia. Also, in European application 66,212 rhodium on alumina in the presence of butyl ether is disclosed to obtain 15–50% trans, trans-isomer ratio contents, but again the pressures are high (4000 psi) and the reaction times short, leading to difficult reaction product control.

In the catalytic processes for hydrogenating methylene bridged polyphenylamines as described above, the bridged polyphenylamines were purified, i.e., distilled to remove trace impurities and oligomers. Crude polyphenylamines were difficult to hydrogenate presumably because impurities in the feedstock poisoned the catalyst. U.S. Pat. No. 3,959,374 describes a process for the catalytic hydrogenation of methylene bridged polyphenylamine which contained trace impurities and oligomers. More specifically a crude methylenedianiline feed containing these impurities and oligomers is initially treated with hydrogen in the presence of a nickel containing hydrogenation catalyst prior to hydrogenation in the presence of a ruthenium catalyst. The pretreatment overcomes low yields (52.4%) and long reaction times associated with nickel and cobalt. In the absence of the pretreatment, ruthenium catalysts, although commonly used for hydrogenation of purified methylenedianiline, were not suited for hydrogenation of a methylene dianiline feed containing impurities, e.g., isomeric impurities.

SUMMARY OF THE INVENTION

This invention relates to an improved process for the catalytic hydrogenation of methylene bridged polyphenylamines to produce the polycyclohexylpolyamine counterparts using a catalyst containing rhodium metal for the hydrogenation. The improvement in the hydrogenation process to produce a polycyclohexylamine counterpart is achieved by initially contacting the crude methylene bridged polyphenylamine containing oligomers and trace impurities, including the formamide of the methylene bridged polyphenylamine with a hydrogenation catalyst, other than rhodium, and which is not a catalyst poison to rhodium, under conditions sufficient to at least effect partial hydrogenation of the reaction mixture and then after this pretreatment or contact catalytically hydrogenating the polyphenylamine to the polycyclohexylamine counterpart in the presence of a rhodium catalyst. The initial hydrogenation of the crude methylene bridged polyphenylamine is typically carried out with ruthenium as the catalyst and the initial hydrogenation is sufficient to destroy the traces of formamide components in the reaction mixture and to prevent rapid deactivation of the rhodium catalyst during the secondary catalytic hydrogenation.

There are several advantages associated with this process. These include:

an ability to extend the life of the rhodium catalyst for the catalytic hydrogenation of the phenyl groups to the cyclohexyl counter parts in crude methylene bridged polyphenylamines;

an ability to produce a hydrogenated methylenedianiline having a trans,trans-isomer concentration of 40% and less;

an ability to effect hydrogenation of methylenedianiline and other methylene bridged polyphenylamines at relatively low pressures e.g. 1500 psig and lower, and at excellent reaction rates;

an ability to utilize an impure feeds, e.g., one containing oligomers and trace amounts of formamide derivatives of methylene bridged polyphenylamines as a reactant and yet obtain cyclohexyl counterparts in high selectivity;

an ability to obtain a reaction product which is substantially free of by-product oligomers and other heavies; and an ability to use the catalyst for continued periods of time with only modest maintenance or regeneration techniques.

DETAILED DESCRIPTION OF THE INVENTION

The process of this invention involves the catalytic hydrogenation of methylene bridged polyphenylamines to the polycyclohexylamine counterparts utilizing a rhodium catalyst. These methylene bridged polyphenylamines are typically prepared by condensing an aromatic amine with formaldehyde to produce the methylene bridged polyphenylamine. Depending upon the condensation process, methylenediphenylamines and diphenyl diamines are produced with minor coproduction of oligomers; i.e., polyphenylamines containing three or more phenyl groups, typically 3–5 phenyl groups. Additionally, in view of the fact that formaldehyde is used to condense the amines, some additional by-products also produced in minor amount, with the major impurities being N-methylmethylenediphenylamine and the formamide of methylenediphenylamine. It is believed that because of these oligomers and other impurities in crude methylene bridged polyphenylamines, rhodium is deactivated during the hydrogenation process.

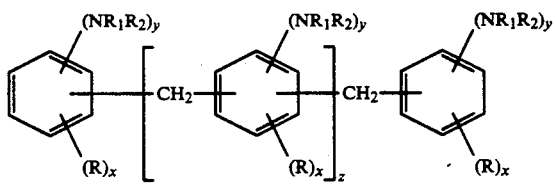

Representative methylene bridged polyphenylamine compositions described by the formula include methylenedianiline; 3,3'-dimethyl-4,4'-diamino-diphenylmethane; 3,3',5,5'-tetramethyl-4,4'diaminodiphenylmethane and 3,3'6,6'tetramethyl-4,4'-diaminodiphenylmethane; 3,3'-ditertbutyl-4,4'-diaminodiphenylmethane and 3,3'-dimethyl-5,5'-ditertbutyl-4,4'-diaminodiphenylmethane; N,N'-dimethy-4,4'-diaminodiphenylmethane, tetramethyl-4,4'-diaminodiphenylmethane; and so forth.

The process involves the pretreatment or initial hydrogenation of a crude polyphenylamine feedstock containing oligomers and trace impurities, such as the formamide of the methylene bridged polyphenylamines, with a hydrogenation catalyst other than rhodium and which is not poisonous to rhodium, under conditions sufficient for effecting at least partial hydrogenation of the feedstock. This initial hydrogenation typically is conducted with a ruthenium catalyst and is carried out for a time sufficient to effect at least substantial decomposition of the formamide impurity in the feedstock. The catalyst usually is incorporated in an amount from 0.0005 to 10% as metal. The initial catalytic hydrogenation must be carried out for a time sufficient to remove sufficient impurities such that substantial deactivation of the rhodium catalyst does not occur during the secondary catalytic hydrogenation of the phenyl groups to the cyclohexyl counterparts. In this way the rhodium catalyst may be used repeatedly for the secondary catalytic hydrogenations without regeneration. Without such initial hydrogenation or pretreatment, the rhodium catalyst must be regenerated more frequently.

If analytical techniques are not available for monitoring the initial catalytic hydrogenation, a guide for initial hydrogenation would suggest that the catalytic hydrogenation using ruthenium catalyst would be in an amount of from about 0.0005 to 15% by weight (as metal) of the methylene bridged polyphenylamine, a reaction time of from 10 to 120 minutes typically 30–60 minutes at temperatures of 130° to 220° C. Shorter periods of time or lower hydrogenation temperatures might result in less removal of trace impurities and also result in slightly higher rates of rhodium catalyst deactivation in the hydrogenation process. If the initial catalytic hydrogenation is carried out over an extended period of time, some partial hydrogenation of the ring may occur and this simply extends the overall reaction time of the combined initial and secondary catalytic hydrogenation processes, but would have no detrimental effect upon catalyst life of rhodium. By effecting at least partial ring hydrogenation in the initial catalytic hydrogenation, one is assured that substantially all of the oligomers or impurities, or both, which are poisonous to the rhodium catalyst are destroyed and therefore catalyst life of rhodium is not adversely affected in the secondary hydrogenation.

As with conventional processes the hydrogenation process is carried out under liquid phase conditions, such liquid phase conditions being maintained typically by carrying out the hydrogenation in the presence of a solvent. Although as reported in the art, it is possible to hydrogenate the feedstock in the absence of a solvent, but the processing is much simpler when a solvent is employed. Representative solvents suited for practicing the invention include saturated aliphatic and alicyclic hydrocarbons such as cyclohexane, hexane, and cyclooctane; low molecular weight alcohols, such as methanol, ethanol, isopropanol; and aliphatic and alicyclic hydrocarbon ethers, such as n-propyl ether, isopropyl ether, n-butyl ether, amyl ether, tetrahydrofuran, dioxane, and dicyclohexylether. Tetrahydrofuran is preferred. Although in some processes water can be used as a cosolvent, it is preferred that the system be maintained in an anhydrous state or at least maintained so that the water concentration is less than 0.5% by weight.

When a solvent is used, it can be used in conventional amounts e.g. concentrations as low as 50% by weight, based on methylene bridged polyphenylamine introduced into the reaction zone; typically the solvent is used at levels from about 75 to about 200% by weight of the starting polyphenylamine. Under some circumstances the solvent is used in amounts as high as 1000 to 2000% based upon the weight of the methylene bridged polyphenylamine.

The initial and secondary hydrogenations of the feed are carried out principally in a batch process although it is possible to operate the plant continuously. Temperatures used for the ring hydrogenation process range from about 130° to 220° C. with preferred temperatures of from about 170° to 195° C. As with prior art hydrogenation processes, hydrogen partial pressures can range from about 500 to 4000 psig. However, in contrast to prior art processes, hydrogen pressures can be as low as from about 700 to 1500 psig, while retaining practical or commercially acceptable reaction rates, the latter processing pressures being preferred for lower equipment and operating costs. Such conditions for hydrogenation using a rhodium catalyst are described in U.S. Pat. No. 3,856,862 and U.S. Pat. No. 3,591,635 and are incorporated by reference.

The ability to hydrogenate methylene bridged polyphenylamines, particularly methylenedianiline, at low hydrogen partial pressures is expanded through the utilization of the pretreatment and a rhodium catalyst preferably a mixed rhodium and ruthenium catalyst system. The rhodium catalyst is broadly used in an amount to provide from 0.001 to 10% by weight of the aromatic amine. This mixed catalyst system permits kinetic control of the isomer mixtures produced by the reaction at low pressures, the ease of reaction being unexpectedly superior to the ease of reaction noted with the rhodium catalyst alone in an unpurified methylene bridged polyphenylamine feed. The catalysts can be added to the reactor individually or they may be physically admixed or combined and used as a single component. To simplify preparation and processing it is preferred to admix the two catalysts and incorporate them into the reaction medium as an admixture. The catalysts are combined, based upon their weights as metal, in a ratio of about 1 to 12 weight parts rhodium per weight part of ruthenium, preferably 4 to 8 parts rhodium per part ruthenium. As the concentration of rhodium increases vis-a-vis ruthenium the activity of the catalyst system increases and therefore lower temperatures or catalyst concentrations may be satisfactory.

The catalysts used and practiced in this invention generally are supported upon an inert carrier and representative carriers include carbon, calcium carbonate, rare earth oxides, such as cerium, praseodymium, or lanthanum; rare earth oxides or carbonates; alumina; barium sulfate; kieselguhr; pumice; titania; diatomaceous earth; and alkaline earth components such as calcium sulfate, calcium oxide, barium oxide, and barium sulfate. Preferred support materials are alumina and titania with titania being preferred. The catalyst usually comprises from about 1 to 25 weight parts metal/weight part of support.

To maintain high activity of the catalyst system in the hydrogenation process it is proposed that at least the rhodium component of the catalyst be alkali moderated. Alkali moderation techniques to produce the catalyst system are well known and the techniques disclosed in U.S. Pat. No. 3,636,108 for the alkali moderation of ruthenium can be utilized for the production of rhodium. Such method is incorporated by reference. Typically, such alkali moderation involves the treatment of the catalyst and support material with an alkali metal hydroxide such as, sodium, lithium or potassium hydroxide or alkali metal alkoxide such as sodium, lithium, or potassium methoxide or ethoxide in an amount to provide from 0.1 to 15% by weight of a basic metal compound calculated as alkali metal. Often, moderation of the catalyst is done prior to reduction of the catalyst with aqueous dilute alkali metal hydroxide during or following metal deposition on the chosen support. Alkali moderation can also be accomplished in situ during hydrogenation by including alkali metal hydroxide, alkali metal alkoxide or by the addition of ammonia. For purposes of practicing this invention it is preferred that the catalyst is alkali moderated prior to reduction and maintained in situ with additions of alkali metal hydroxide.

The progress of the secondary hydrogenation reaction can readily be followed by observing the amount of hydrogen taken up by the reaction mixture. The reaction is terminated when the amount of hydrogen absorbed is equal to that amount necessary to effect complete hydrogenation of the product. In general, the hydrogenation time will range from about 45 to 900 minutes, at catalyst levels, e.g., 0.5-2.5% catalyst by weight of the methylene bridged polyphenylamine and generally will not exceed 300 minutes. The reaction time can be adjusted to adjust isomer selectivity as in the case of methylenedianiline.

The following examples are intended to illustrate various embodiments of the invention and all parts and percentages given are weight parts or weight percents unless otherwise specified.

EXAMPLE 1

Crude Methylenedianiline (MDA) Pretreatment

A 300 cc autoclave was charged with a solution of 62.4 g of undistilled, i.e., crude methylenedianiline (MDA) [(85% MDA, 15% MDA oligomers, and trace amounts of the formamide of methylenedianiline and other by-products)] in 87.6 g of tetrahydrofuran (THF) and 0.1 g of catalyst consisting of 5% ruthenium on alumina. The autoclave was purged with nitrogen followed by hydrogen. The autoclave was then pressurized to about 700 psig with hydrogen and heated to 192° C. After this temperature was reached, the autoclave was maintained at 850 psig by addition of hydrogen from a ballast tank. The autoclave was held at 192° C. for 100 min. Very little hydrogen had been consumed in this time. The autoclave was then cooled and vented. The GC analysis of the reactor effluent showed about 6% of the MDA had one ring hydrogenated. Neither the formamide of methylenedianiline nor fully hydrogenated methylenedianiline was seen in the product.

EXAMPLE 2

Comparison Effect of Pretreatment

In this example 5 runs were made for comparison purposes. Run A illustrates the effectiveness of Rh and Run B illustrates the effectiveness of a Rh/Ru catalyst with the initially pretreated or hydrogenated feed of Example I. Runs C and D illustrate the limited effectiveness of Rh and Rh/Ru catalysts with crude MDA i.e., MDA which has not been pretreated and therefore containing trace oligomers and the formamide of methylenedianiline. Run E illustrates pretreatment of crude MDA feed with a Ni hydrogenation catalyst.

In Runs A and B a 300 cc autoclave was charged with 125.6 g of the effluent from Example 1. The catalyst was added along with 0.07 g of 10% by weight LiOH in water. The autoclave was sealed and purged with nitrogen followed by hydrogen addition. The autoclave was then pressurized to about 700 psig with hydrogen and heated to 192° C. At 192° C., the autoclave pressure was kept at 850 psig by addition of hydrogen from a ballast tank. In both Runs A and B hydrogen uptake was noticed by the time the temperature of 192° C. was reached. The autoclave was cooled after the reaction was estimated to be completed.

For runs C & D, a 300 cc autoclave was charged with 125 g of 42% by weight crude MDA. The catalyst, along with 0.07 g of 10% by weight LiOH in water, were added. The autoclave was sealed and flushed with nitrogen followed by hydrogen. The autoclave was pressurized to about 600 psi with hydrogen was heated to 192° C. with agitation. Once the temperature of 192° C. was reached, the autoclave pressure was maintained at 850 psig by addition of hydrogen throughout the reaction from a ballast tank. With the Rh catalyst, no hydrogen uptake was noticed for about 400 min. About 20% of the theoretical hydrogen was consumed in about 500 min. The reaction was complete in 920 min.

With the Rh/Ru catalyst, the 10% theoretical hydrogen uptake took 36 min. and the reaction was complete in 200 min.

As for Run E, a 300 cc autoclave was charged with a crude MDA/THF solution as in Example 1. Then, 1 g of Raney Ni 2800 was added and the autoclave sealed and purged with nitrogen. This was followed by addition of hydrogen. The reactor was pressurized with hydrogen to about 700 psig then heated to 200° C. Hydrogen pressure was maintained at 850 psig by addition of hydrogen from a ballast tank. About 10% of the theoretical hydrogen was consumed in 2 hr at which time the reaction had ceased. GC analysis of the reactor effluent showed about 23% of the MDA had one ring hydrogenated. No MDA formamide derivative were noted in the initially hydrogenated feed. The reactor was filtered to remove the Ni catalyst. The filtrate was charged into a clean 300 cc autoclave along with 0.73 g of 5% Rh on alumina and 0.09 g of 5% Ru on alumina. Then 0.08 g of 10% LiOH in water was added and the autoclave sealed and purged with nitrogen. After purging hydrogen was added. The autoclave was pressurized with hydrogen to about 700 psig then heated to 192° C. Hydrogen uptake was noticed at about 160° C. and the hydrogen ballast tank was opened to maintain the autoclave pressure at 850 psig. The rate of hydrogen uptake dropped rapidly and became only one-fourth the initial rate in 45 minutes. The reaction was terminated after 300 minutes even though only 91% of the expected hydrogen uptake had occurred. The failure of the reaction to complete was verified by analysis of the product which showed 18% half hydrogenated MDA. Hydrogen uptake slowed rapidly and had apparently ceased after about 300 min. Results of Runs A-E are included in Table 1.

TABLE 1

| Feed | Catalyst | Pre-treatment | Reaction Time (min) | % Conversion* | % Yield** | % t,t Isomer |
|---|---|---|---|---|---|---|
| Run A | 0.72 g Rh# | Yes | 250 | 100 | 87.5% | 23.2 |
| Run B | 0.72 g Rh# 0.09 g Ru# | Yes | 145 | 93 | 89.8 | 14.1 |
| Run C | 0.72 g Rh# | No | 920 | 100 | 91.0 | 28.9 |
| Run D | 0.72 g Rh# 0.09 g Ru# | No | 200 | 100 | 91.2 | 16.1 |
| Run E | 0.72 g Rh# 0.09 g Ru# | No | 300## | 91 | 77.8 | 28.5 |

*Conversion based on observed consumption of hydrogen versus theory
**Yield as PACM and half hydrogenated MDA based on MDA in feed
Catalysts were 5% metal on an alumina support
Reaction had stopped As can be seen from the above data, excellent reaction rates were obtained through the use of a rhodium catalyst (Run A) and through the use of a mixed Rh/Ru metal catalyst (Run B) where the feed was initially pretreated or hydrogenated as compared to a non-pretreated feed. Compare Runs A and C and Runs B and D. Run B, which was terminated early (93% conversion), shows the mixed metal catalyst was more effective than the Rh catalyst alone. The nickel pretreatment in Run D was effective in reducing contaminants, e.g., the formaldehyde of MDA in the crude MDA feed but the Ni catalyst adversely affected the reactivity of the Rh/Ru catalyst system or poisoned it to the point where the catalyst was ineffective in the secondary hydrogenation step. As a result, the reaction failed to complete leaving 18% half reduced MDA.

EXAMPLE 3

Catalyst Deactivation Study

This example illustrates the improved retention of catalyst activity during reuse when the crude MDA feed is pretreated or initially hydrogenated using a hydrogenation catalyst which is not a catalyst poison to rhodium, e.g. Ru.

A pretreated feed used in this example was prepared by the technique used in Example 1. A crude MDA/THF solution (2000 g) was charged into a 1 gal autoclave along with 12.5 g of 5% Ru on alumina catalyst. After nitrogen and hydrogen purging, the autoclave was heated to 195° C. under 850 psig pressure by hydrogen addition. The temperature was maintained for 30 min after which the autoclave was cooled and vented. The reactor effluent was filtered to remove the catalyst. Secondary hydrogenations were made reusing a single charge of catalyst (1.5% catalyst based on the weight of crude MDA). In a first series of 7 runs the pretreated crude MDA/THF feed was hydrogenated with a catalyst which was 80% by weight of 5% Rh on alumina and 20% of 5% Ru on alumina. In a second series of 7 runs, crude MDA/THF which had not been pretreated or initially hydrogenated was hydrogenated with a catalyst which was 89% by weight of 5% Rh on alumina and 11% of 5% Ru on alumina. The reactions were run at approximately 180° C. until completion as estimated by hydrogen uptake. The results are shown in Table 2.

TABLE 2

| Pretreated | Use | Reaction Time* | Conversion** | Yield# | t,t Isomer |
|---|---|---|---|---|---|
| Yes | 1 | 200 min | 99% | 88.2% | 19.2% |
| Yes | 2 | 240 | 99 | 87.8 | 19.2 |
| Yes | 3 | 190 | 100 | 89.2 | 25.1 |
| Yes | 4 | 190 | 99 | 92.8 | 21.4 |
| Yes | 5 | 230 | 100 | 93.8 | 21.8 |
| Yes | 6 | 230 | 98 | 96.1 | 21.2 |
| Yes | 7 | 245 | 98 | 94.9 | 21.9 |
| No | 1 | 300 | 100 | 88.3 | 21.5 |
| No | 2 | 330 | 90 | 91.6 | 14.3 |
| No | 3 | 370 | NO ANALYSIS | — | |
| No | 4 | 405 | 100 | 93.9 | 20.1 |
| No | 5 | 510 | 100 | 96.5 | 20.4 |
| No | 6 | 585 | 90 | 98.9 | 21.2 |
| No | 7 | 720 | 100 | 98.8 | 26.9 |

*Time at 180° C., reaction may not be complete
**Conversion based on hydrogen consumption versus theory
Yield based on available MDA, includes PACM and one ring reduced MDA As can be seen from the data in Table 2 pretreatment of crude MDA to remove the formamide of MDA and possibly other contaminants via an initial hydrogenation substantially enhanced rhodium catalyst life as compared to hydrogenation of crude MDA containing oligomers and formamide using a similar rhodium containing catalyst. Thus, the pretreatment improves reactivity of the catalyst and clearly extends catalyst life.

Although not intending to be bound by theory it is believed the initial pretreatment or hydrogenation is effective because it destroys an impurity in the feed. It is believed this impurity is the formamide of MDA and it acts as a poison to Rh. Besides inhibiting the Rh catalyst, this impurity most likely causes loss in Rh activity which is not reversed under reaction conditions. This deactivation is believed to be due to Rh oxidation.

What is claimed is:

1. In a process for the hydrogenation of a crude methylene bridged polyphenylamine feed containing oligomers to produce the corresponding methylene bridged polycyclohexylamine counterpart in the presence of a rhodium hydrogenation catalyst at a temperature and for a time sufficient to effect hydrogenation of the phenyl ring to the cyclohexyl ring, said methylene bridged-polyphenyl amine feed represented by the formula:

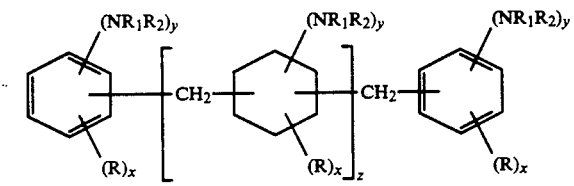

wherein R is $H_1$, $C_{1-6}$ alkyl, $C-O-R_3$, where $R_3$ is $C_{1-4}$ alkyl, $CH_2NH_2$, $R_1$ and $R_2$ are H or $C_{1-6}$ alkyl, x is 1-4, y is 0 to z with the sum being at least 1, provided that $x+y$ is not greater than 5, and z is from 0 to 3 pretreating the crude methylene bridged polyphenylamine feed via an initial hydrogenation in the presence of hydrogen and a hydrogenation catalyst consisting essentially of ruthenium under conditions sufficient to at least partially hydrogenate the feed, and then catalytically hydrogenating the methylene bridged polyphenylamine in a secondary hydrogenation zone containing rhodium catalyst for producing the corresponding methylene bridged polycyclohexylamine counterpart.

2. The process of claim 1 wherein said initial hydrogenation is carried out using ruthenium as the hydrogenation catalyst.

3. The process of claim 2 wherein said initial hydrogenation is carried out at at temperature from 130° to 220° C. and for a time from about 10 to 120 minutes.

4. The process of claim 3 wherein the ruthenium, as metal, is present in an amount of from 0.0005 to 10% by weight as metal of the methylene bridged polyphenylamine.

5. The process of claim 4 wherein each x is 1 and each y is 1.

6. The process of claim 5 wherein $R_1$ and $R_2$ are hydrogen.

7. The process of claim 6 wherein R is hydrogen or methyl.

8. The process of claim 7 wherein z is 0.

9. The process of claim 8 wherein R is hydrogen.

10. The process of claim 9 wherein the catalytic hydrogenation of the methylene bridged polyphenylamine to methylene bridged polycyclohexylamine is carried out using rhodium where the rhodium is present in an amount of from 0.001 to 10% by weight as metal of the methylene bridged polyphenylamine.

11. The process of claim 10 wherein ruthenium is added to the rhodium in the secondary hydrogenation zone and the ratio of rhodium to ruthenium is from about 2-12 weight parts rhodium per weight part ruthenium.

12. The process of claim 4 wherein said methylene bridged polyphenylamines are selected from the group consisting of methylenedianiline; 3,3'-dimethyl-4,4'-diaminodiphenylmethane; 3,3'5,5'-tetramethyl-4,4'diaminodiphenylmethane, 3,3'6,6'-tetramethyl-4,4'-diaminodiphenylmethane; 3,3'-di-tert-butyl-4,4'-diaminodiphenylmethane; 3,3'-dimethyl5,5'-di-tert-butyl-4,4'-diaminodiphenylmethane; N,N'-dimethyl-4,4'-diaminodiphenylmethane; and tetramethyl-4,4'-diaminodiphenylmethane.

13. The process of claim 12 wherein said methylene bridged polyphenylamine is methylenedianiline.

14. The process of claim 12 wherein said methylene bridged polyphenylamine is 3,3'4,4'-diaminodiphenylmethane.

15. The process of claim 12 wherein said methylene bridged polyphenylamine is 3,3'-di-tert-butyl-4,4'-diaminodiphenylmethane.

16. The process of claim 12 wherein said methylene bridged polyphenylamine is 3,3'6,6'-tetramethyl-4,4'-diaminodiphenylmethane.

* * * * *